United States Patent [19]

Dalton et al.

[11] Patent Number: 4,803,072
[45] Date of Patent: Feb. 7, 1989

[54] IMMUNOMODULATION

[75] Inventors: Barbara J. Dalton, Philadelphia, Pa.; Robert C. Rees, Sheffield, England

[73] Assignee: SmithKline Beckman Corporation, Philadelphia, Pa.

[21] Appl. No.: 905,825

[22] Filed: Sep. 10, 1986

[51] Int. Cl.$^4$ ..................... A61K 45/02; A61K 37/02
[52] U.S. Cl. .................... 424/85.5 C; 514/2; 514/12
[58] Field of Search ............... 424/85, 86, 89; 435/68, 435/811; 514/2, 12

[56] References Cited

FOREIGN PATENT DOCUMENTS 0176493  4/1986  European Pat. Off. .

OTHER PUBLICATIONS

Bishop et al., *J. Immunol*, 131, 1849 (1983).
Casali et al., *J. Exp. Med.*, 54, 840 (1981).
Harfast et al., *Scand. J. Immunol.*, 11, 391 (1985).
Alsheikhly et al., *Scan. J. Immunol.*, 17, 129 (1983).
Arora et al., *J. Virology*, 52, 389 (1984).
Ali et al., *Immunol.*, 52, 687 (1984).
Djeu et al., *J. Exp. Med.*, 156:1222 (1982).
Starr et al., *Infection and Immunity*, 30:17 (1980).
Shaw et al., *J. Exp. Med.*, 156, 243 (1982).
Morrongiello et al., *Intervirology*, 8, 281.
Young et al., "The Origin of Pandemic Influenza Viruses", W. G. Laver, editor, Elsevier Science Publishing Co., Inc. (1983), 129–137.
Young et al, *Proc. Natl. Acad. Sci., U.S.A.*, 80, 6105–6109 (1983).
Shaw et al., *Infection and Immunity*, 34(3), 1065–1067.
Tiensiwakul et al., *Intervirology*, 20, 52–55 (1983).

*Primary Examiner*—Blondel Hazel
*Attorney, Agent, or Firm*—Carol G. Canter; Edward T. Lentz; Alan D. Lourie

[57] ABSTRACT

An immunomodulating pharmaceutical composition comprising an effective, leukocyte interferon production inducing amount of NS1 and a pharmaceutically acceptable carrier or diluent; and a method of modulating the immune response in a human or other animal in need thereof by inducing the production of leukocyte IFN which comprises administering an effective amount of NS1 to such human or animal.

11 Claims, No Drawings

IMMUNOMODULATION

BACKGROUND OF THE INVENTION

This invention relates to a method of modulating the immune response in a human, or other animal, in need thereof by inducing the production of interferon (IFN) by leukocytes which comprises administering an effective amount of influenza A NS1 to such human or animal; and to an immunomodulating pharmaceutical composition comprising an effective, leukocyte interferon production inducing amount of NS1 and a pharmaceutically acceptable carrier or diluent.

Several studies using virus systems have shown that virions, and in some instances isolated viral proteins, can enhance natural cytotoxicity. [See, e.g., Bishop et al., *J. Immunol.*, 131, 1849 (1983); Casali et al., *J. Exp. Med.*, 54, 840 (1981); Harfast et al., *Scand. J. Immunol.*, 11, 391 (1985); Alsheikhly et al., *Scand. J. Immunol.*, 17, 129 (1983).] Using the influenza virus glycoproteins (haemagglutinin and neuraminidase components), enhanced natural cytotoxicity of human peripheral blood mononuclear cells (PBMC) was demonstrated. [See, Arora et al., *J. Virology*, 52, 389 (1984).] This contrasts with recent observations that subunit influenza virus haemagglutinin, prepared by detergent solubilization, profoundly and irreversibly inhibits human natural cytotoxicity against K562 targets. [See, Ali et al., *Immunol*, 52, 687 (1984).] The results of these studies suggest that different molecular structures may mediate these different or diverse biological effects, although a more precise definition of the mechanisms involved is needed.

It has been shown that virus-infected target cells are extremely sensitive to NK-mediated lysis. This enhancement of lytic activity is thought to be mediated by endogenously produced IFN, but it is not established whether IFN from the infected target or the effector cell population is responsible for increasing cytotoxicity, although it is recognized that human NK cells can produce IFN upon appropriate stimulation. Human NK cells enriched by discontinuous Percoll density gradient separation can be stimulated by intact virus particles (influenza A and HSV-1, NDV and Sendai viruses) to release IFN, mainly IFNα, although the production of IFNγ has been observed with lymphocytes isolated from individuals seropositive for influenza A or CMV virus incubated with homologous viral antigen. [See, Djeu et al., *J. Exp. Med.*, 156: 1222 (1982) and Starr et al., *Infection and Immunity*, 30: 17 (1980)]. In contrast, it was recently shown that detergent solubilized influenza virus haemagglutinin (HA) causes a profound and irreversible depression in human NK cytotoxicity. [See, Ali et al., *Immunol.*, 52: 687 (1984)].

The function of NS1 and NS2 nonstructural proteins during influenza A viral infection is unclear. It is interesting to note that NS1 has been detected on the surface of virus infected cells [See, Shaw et al., *J. Exp. Med.*, 156, 243 (1982)], and, it has been demonstrated serologically that extensive cross-reactivity exists between NS1 proteins from influenza A virus strains of human, avian, porcine and equine origin. [See, Shaw et al., cited above and Morrongiello et al., *Intervirology*, 8, 281 (1977).]

Young et al., "The Origin of Pandemic Influenza Viruses", W. G. Laver, editor, Elsevier Science Publishing Co., Inc. (1983), 129–137, review the cloning and expression of influenza virus genes and disclose the expression of the NS1 protein in bacteria cells (*E. coli* strain N99) transformed with a pAS1 expression vector containing the NS gene of influenza virus strain A/PR/8/34 (H1N1).

Young et al., *Proc. Natl. Acad. Sci., U.S.A.*, 80, 6105–6109 (1983), disclose the expression of the NS1 protein by cells of *E. coli* strain N5151 transformed with a pAS1 expression vector containing the NS gene of influenza virus strain A/PR/8/34 (H1N1). Young et al. also disclose that the protein expressed by the NS gene was extracted, purified and injected into rabbits whose serum was subsequently used for immunoprecipitation and immunofluorescence assays.

Shaw et al., *J. Exp. Medicine*, 156, 243–254 (1982), disclose the purification of NS1 from cytoplasmic inclusions that were solubilized and used to raise antisera in rabbits; and also disclose that NS1 appeared to be highly conserved in different influenza A virus isolates. Shaw et al. state that since the NS1 antigen is expressed on the surface of infected cells, this suggests that an immune response to this protein could conceivably be of importance. Furthermore, Shaw et al. state that since there is extensive cross-reactivity in the NS1 proteins produced by different influenza A virus serotypes, NS1 related antigens should be considered as possible targets for cross-reactive cytotoxic T cells generated during infection.

Shaw et al., *Infection and Immunity*, 34(3), 1065–1067 (1981), disclose that the influenza A virus 23,000 dalton nonstructural protein, NS1, can be detected by direct immunofluorescence on the surfaces of infected mouse cells as early as 4 hours after infection with the A/WSN (H1N1) strain of influenza A virus. Shaw et al. conclude that since their results strongly suggest the surface expression of NS1 protein or a structurally related molecule on influenza A virus-infected cells, and since antigenic cross-reactivity has been shown for nonstructural antigens induced by different influenza A serotypes, NS1-related antigens should be considered as possible targets for cross-reactive cytotoxic T cells generated during influenza A virus infection.

Djeu, *Clin. Immunol. Allerg.*, 3(3), 561–568 (1983), reviews the production of interferon by human natural killer (NK) cells and discloses that a large number of biological agents, including influenza virus strain A/PC, induce the production of interferon (IFN) by natural killer cells. Djeu also states that "since a vast array of biological agents can induce rapid IFN production by NK cells, it is tempting to speculate that the first step in defense (sic) against invading agents is the production of IFN which produces self-activation of NK activity in LGL (NK cells)."

Tiensiwakul et al., *Intervirology*, 20, 52–55 (1983), disclose that purified adenovirus fiber protein (FP) (a B-cell mitogen) induced the synthesis of interferon in murine cells.

SmithKline Beckman Corporation, European patent application Publication No. EPO, 176,493 A1, published Apr. 2, 1986, claims a vaccine for stimulating protection in animals against infection by influenza virus which comprises a polypeptide, other than an HA protein, having an immunogenic determinant of the HA2 subunit of an HA protein, wherein the immunogenic determinant is carried on a fusion protein having the N-terminal of the HA2 subunit fused to about 80 N-terminal amino acids of the NS1 protein which carries the HA2 subunit to assume an immunogenic configuration. SmithKline Beckman Corporation also disclose the cloning and expression of a coding sequence for the influenza A virus matrix protein.

SUMMARY OF THE INVENTION

This invention relates to the discovery that the NS1 protein of influenza A virus can induce production of leukocyte interferon in an animal. More particularly, this invention relates to an immunomodulating pharmaceutical composition comprising an effective, leukocyte interferon production inducing amount of NS1 and a pharmaceutically acceptable carrier or diluent.

This invention also relates to a method of modulating the immune response in a human, or other animal, in need thereof by inducing the production of IFN by such human or other animals leukocytes which comprises administering an effective leukocyte interferon production inducing amount of NS1 to such human or other animal.

DETAILED DESCRIPTION OF THE INVENTION

By the term "leukocyte" is meant any circulating or tissue nonerythroid nucleated white blood cell.

Examples of such leukocytes include natural killer cells ("NK cells"), peripheral blood mononuclear cells ("PMBC"), monocytes, macrophages, polymorphonuclear cells and lymphocytes (e.g., B cells, T cells, NC cells, K cells, null cells).

Using recombinant DNA technology, cDNA copies of the 8 influenza A virus genomic RNA segments have been cloned, and several of these genes have been expressed into *Escherichia coli* (*E. coli*) plasmid vectors. This method permits the production and isolation of individual viral components and derivatives which would otherwise not be available. A number of cloned influenza viral gene products were evaluated for their ability to influence human NK cell activity. The studies showed that the NS1 protein, as well as fusion products containing a portion of the NS1 protein, induce the production of IFN by leukocytes such as NK cells.

As used herein, the term "NS1" means the polypeptide derived from the 230 amino acid coding sequence of the NS1 gene of influenza A virus or any functional derivative thereof. By the term "functional derivative" is meant fusion constructs containing a portion of the NS1 coding sequence linked to some other polypeptide coding sequence, such as but not limited to the haemagglutinin or matrix protein coding sequence, wherein said fusion polypeptide coding sequence is capable of inducing sufficient leukocyte interferon production to augment the immune response in an animal in need thereof. Preferably such fusion constructs contain at least about 80 N-terminal amino acids of NS1 linked either at the C or N terminus to a polypeptide coding sequence such as but not limited to some portion of the haemagglutinin or matrix protein coding sequences. The haemagglutinin (HA) protein coding sequence of the influenza A virus is known. See, e.g., Winter et al., *Nature*, 292, 72-75 (1981), who report a DNA coding sequence for HA of the influenza A virus strain A/PR/8/34 strain (H1N1). The HA gene product can be prepared synthetically or can be derived from influenza A virus RNA by known techniques. See, e.g., Emtage et al., U.S. Pat. No. 4,357,421, who disclose the cloning and expression of a coding sequence for an influenza A virus HA gene. Also, various influenza A virus strains are available from clinical specimens and from public depositions such as those available from the American Type Culture Collection, Rockville, Md., U.S.A. The matrix protein coding sequence of the influenza A virus is known. See, e.g., Winter et al., *Nucl. Acids Res.*, 8, 1965-1974 (1980). The matrix protein coding sequence product can be prepared synthetically or can be derived from influenza A viral RNA by known techniques. See, e.g., SmithKline Beckman Corporation, European patent application Publication No. EP 0,176,493 A1, who disclose the cloning and expression of a coding sequence for matrix protein.

Such fusion constructs can be prepared by conventional techniques. For example, plasmids containing cDNA copies of the viral RNAs of influenza A virus strain A/PR/8/34 [see, Young et al., The Origin of Pandemic Influenza Virus, Laver (Ed.), Elsevier Press, Amsterdam, p. 120 (1983)] can be manipulated as described in SmithKline Beckman Corporation, European patent application Publication No. EP 0,176,493 A1 to produce the N-terminal 81 amino acids of NS1 fused to the matrix protein coding sequence or fused to the HA coding sequence.

By the term "functional derivative" is also meant those derivatives of NS1 which substantially retain the leukocyte interferon inducing capacity of NS1. Such derivatives include, but are not limited to, functional derivatives prepared by the addition, deletion or substitution of any of the amino acids comprised by the NS1 coding sequence, and functional derivatives which are complexes of NS1 with other compounds or molecules. Such derivatives can be prepared by conventional techniques. However, it should be noted that a DNA fragment comprising only the first 81 amino acids of the NS1 coding sequence did not retain the leukocyte interferon inducing capacity of the NS1 gene product. Thus, the term "functional derivative" as used herein does not include a DNA fragment consisting essentially of the first 81 amino acids of the NS1 coding sequence.

The coding sequence of NS1 is known. See, e.g., Baez et al., *Nucl. Acids Res.*, 8, 5845-5857 (1980), who report a DNA coding sequence for the nonstructural (NS) protein of influenza A virus strain A/PR/8/34. NS1 can be prepared synthetically or can be derived from influenza A viral RNA by known techniques. See, e.g., Young et al., *Proc. Natl. Acad. Sci. USA*, 80, 6105-6109 (1983), who report cloning of cDNA from all eight RNA segments from influenza A virus strain A/PR/8/34 in *E. coli* and also report high level expression of the NS1 protein in *E. coli*. Also, various influenza A virus strains are available from clinical specimens and from public depositories, such as the American Type Culture Collection, Rockville, Md., U.S.A. Systems for cloning and expressing the NS1 gene product in various microorganisms and cells, including, for example, *E. coli*, Bacillus, Streptomyces, Saccharomyces, and mammalian and insect cells are known and are available from private and public laboratories, depositories and commercial vendors.

Interferon (IFN) has been shown to be a major component in determining the cytotoxicity status of natural killer (NK) cells both in vivo and in vitro. Other effects ascribed to interferons include their ability to augment macrophage and monocyte cytotoxicity, stimulate lectin-induced cytotoxicity and enhance antibody-dependent cell-mediated cytotoxicity (ADCC). This positive regulation of the host defenses may prove important as an in vivo mechanism for maintaining and promoting resistance against neoplasia and infection. Compounds which augment NK activity, such as poly I:C and *C.*

*parvum*, are, in the main, potent inducers of IFN, although some agents, such as Interleukin II (IL-2), appear to augment NK cytotoxicity independent of the induction of detectable interferon levels.

The induction of leukocyte interferon production in an animal in need thereof leads to an augmentation of the cytotoxic activity of natural killer cells in such animal and is useful for the prophylactic treatment of malignant tumor metastasis, and viral and fungal diseases (See, Herberman, R. B. (Ed.), "NK Cells and Other Natural Effector Cells", Academic Press, 1982); or for the therapeutic treatment of malignant tumor metastasis, and viral and fungal infections (See, "NK Cells and Other Natural Effector Cells", cited above). The stimulation of the production of leukocyte IFN in a human or animal in need thereof is also useful for the prophylactic treatment of malignant neoplasms and organ metastasis, certain bacterial, viral or fungal infections; veterinary diseases (e.g. shipping fever), [See, e.g., Finter (Ed.), "Interferon 4: In Vivo and Clinical Studies"; Elsevier (1985)]; or for the therapeutic treatment of some types of cancer (leukemias, lymphomas, papillomas, sarcomas and carcinomas) as well as life threatening viral infections.

It has now been found that NS1 induces the production of IFN in leukocytes such as peripheral blood mononuclear cells (PBMC) which results in augmented human natural killing against a variety of target cell lines. The NS2 gene product did not have such effect. To determine the effect of the NS1 antigen, the A375 melanoma cell line was employed. The A375 melanoma cell line proved to be a reliable indicator cell for detecting enhanced natural cytotoxicity, and was relatively insensitive to spontaneous PBMC killing, and allowed discrimination between natural and activated cytotoxicity.

In summary, it has now been found that: (a) NS1 or a functional derivative thereof, such as the protein product of fusion constructs containing the N-terminal 81 amino acid sequence of the NS1 coding sequence linked to haemagglutinin or matrix protein sequences, induce IFN production by nylon wool non-adherent PBMC which augments natural-cell-mediated-cytotoxicity; (b) neither the induction of IFN nor augmentation of natural cytotoxicity by these stimulatory antigens is correlated with the presence of contaminating bacterial lipopolysaccharide or nucleic acid; (c) the majority of IFN released from PBMC by these stimulatory antigens was IFN$\alpha$ although 2–10% of the detectable interferon was IFN$\gamma$; (d) the augmentation of natural cytotoxicity by these stimulatory antigens was mediated through the release of IFN$\alpha$, as shown by neutralization studies using specific anti-IFN$\alpha$ and anti-IFN$\gamma$ antisera; (e) PBMC fractionating in the low density regions on discontinuous percoll density gradients were shown to release IFN and to respond to IFN. The findings listed above suggest that blood monocytes and adherent lymphoid cells are not required for either IFN production or NK cell activation upon NS1 antigen stimulation; indeed, the presence of adherent cells appeared to be inhibitory to IFN production in vitro.

Although it is apparent from the findings listed above that the observed enhanced natural cytotoxicity of leukocytes such as NK cells is mediated primarily through the production of IFN$\alpha$, it is conceivable that augmentation of cytotoxicity is the result of synergy between IFN$\alpha$ and other molecules present in culture supernatant. For example, recent reports have shown that interleukin 2 (IL-2) is a potent stimulator of NK cell cytotoxicity. To determine whether or not other molecules present in the culture supernatant were acting in synergy with the IFN$\alpha$ produced by NS1 antigen stimulation, supernatants derived from 18-hour PBMC cultures, incubated in the presence or absence of NS1 antigen, were assayed for the presence of IL-2 activity against a human IL-2 dependent target (CTLL-20 cell line). There was no indication of the presence of IL-2 in culture supernatants from PBMC stimulated with NS1, and such findings lead to the conclusion that the observed enhancement of natural cytotoxicity by NS1 antigen stimulation is independent of IL-2 production.

This invention relates to an immunomodulating pharmaceutical composition comprising an effective, leukocyte interferon production inducing amount of NS1 and a pharmaceutically acceptable carrier or diluent. Such composition may be prepared by conventional techniques. For example, a pharmaceutical composition of this invention suitable for parenteral administration is prepared by admixing a desired amount of NS1 in sterile isotonic solution which is pH adjusted with an appropriate buffer to a pH of about 6.0. As another example, a pharmaceutical composition of this invention suitable for administration by inhalation is prepared by admixing a desired amount of NS1 with ethanol to obtain a solution (not to exceed 35% ethanol) which is then combined with a propellant, such as, but not limited to, a mixture of Freon 12 and 114, and a surfactant, such as, but not limited to, Span 85.

This invention also relates to a method of modulating the immune response in a human, or other animal, in need thereof by stimulating the production of leukocyte IFN which comprises administering an effective amount of NS1 to such human or other animal. An effective leukocyte interferon production inducing amount of NS1 can be administered to such human or animal in a conventional dosage form prepared by combining such amount with a conventional pharmaceutically acceptable carrier or diluent according to known techniques. See, e.g., U.S. patent application Ser. No. 759,785, filed July 29, 1985. It will be recognized by one of skill in the art that the form and character of the pharmaceutically acceptable carrier or diluent is dictated by the amount of active ingredient with which it is to be combined, the route of administration and other well-known variables. NS1 is administered to a human or other animal in need of immunomodulation in an amount sufficient to enhance the production of leukocyte IFN in such human or animal to an immune system augmenting extent. The route of administration may be oral, parenteral or by inhalation. The term parenteral as used herein includes intravenous, subcutaneous, intraperitoneal, rectal, vaginal, intramuscular and intralesional forms of administration. The daily oral or parenteral dosage regimen of NS1 will be from about 0.05 to about 1.0 mg per kilogram (kg) of total body weight, preferably from about 0.05 to about 0.25 mg/kg. The term "inhalation" as used herein includes intranasal and oral inhalation administration. Appropriate dosage forms for such administration, such as an aerosol formulation or a metered dose inhaler, may be prepared by conventional techniques. The preferred daily dosage amount of NS1 is from about 0.5 mg/kg to about 1.0 mg/kg when administered by inhalation. It will be recognized by one of skill in the art that the optimal quantity and spacing of individual dosages of a leukoycyte interferon production inducing amount of NS1 will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a leukocyte interferon production inducing amount of NS1 given per day for a defined number of days, can be ascertained by those skilled in the art using conventional course of treatment determination tests.

EXAMPLES

Without further elaboration, it is believed that one skilled in the art can, using the preceding description, utilize the present invention to its fullest extent. The following Examples are, therefore, to be construed as merely illustrative and not a limitation of the scope of the present invention in any way. All temperatures are in degrees centigrade (Celsius).

MATERIALS AND METHODS

I.

NK-Cell-Mediated Cytotoxicity (a) Target Cells

The target cells used in the NK-cell-mediated cytotoxicity assay were the myeloid leukemia K562 cell line [See, Lozzio et al., Blood, 45, 326 (1975)], the adherent human melanoma cell line A375, two colorectal carcinoma lines (SW742 and COLO205) and the RAJI (Burkitt's lymphoma) cell line. K562 and RAJI cells were grown as suspension cultures in RPMI 1640 medium supplemented with 10% fetal calf serum (RPMI-FCS) and were subcultured as necessary. RPMI medium is available from M. A. Bioproducts, Walkersville, Md. FCS is available from Hyclone Laboratories, Sterile Systems, Logan, Utah. The A375 and COLO205 target lines were grown as monolayer cultures in Eagles minimum essential medium supplemented with 2% essential amino acids, 2% vitamin mix, 1% nonessential amino acids, 1% sodium pyruvate, 1% glutamine (200 mM) and 10% fetal calf serum (complete-C-MEM). The SW742 cells were grown as adherent cells in RPMI-FCS medium. Adherent cell lines were subcultured 1-5 times twice weekly, following disruption of the cell sheet with trypsin-EDTA. All cell lines were mycoplasma-free, and iso-enzyme analysis showed them to be of human origin. Twenty-four hours prior to use in cytotoxicity assay, sub-confluent flasks of A375, and SW742 and COLO205 target cells were subcultured 1 to 2. For use as targets in cytotoxicity tests, the adherent cell lines were removed with trypsin-EDTA, washed twice in RPMI-FCS and labelled with $^{51}$Cr (Na$_2$$^{51}$CrO$_4$).

(b) Effector Cells

Peripheral blood mononuclear cells (PBMC) were separated from heparinized blood (10 Units/ml) from normal healthy individuals by centrifugation on ficoll-hypaque density gradients [See, Boyum, Scand. J. Clin. Lab. Invest. (Suppl.), 21, 77 (1968)]. PBMC recovered from the interface fraction were washed 3 times in RPMI-FCS medium, and except where noted, were loaded onto nylon wool columns [See, Julius et al., Europ. J. Immunol., 3, 645 (1973)]. The non-adherent lymphocytes (50-70% of the input population) were recovered using a modified separation technique [See, Rees et al., Int. J. Cancer, 15, 762 (1975)], washed 3 times in RPMI-FCS medium and used in experiments.

Nylon wool non-adherent PBMC were enriched for large granular lymphocytes using seven-step percoll density gradients that were prepared by the method previously described (40% to 57%) [See, Timonen, J. Immunol. Methods, 51, 269 (1982)]. Effector cells ($5 \times 10^7$ cells in 1.5 ml volume) were layered onto the gradient, which was centrifuged at room temperature at $550 \times g$ for 30 minutes. Interface fractions were collected, washed 3 times in RPMI-FCS medium and used in cytotoxicity assays.

Cytospin preparations of cells recovered from percoll fractions were stained by Giemsa and identified morphologically. Cell types were characterized as large lymphocytes (LL), large granular lymphocytes (LGL), small lymphocytes (SL), monocytes (M) or neutrophils (N) and the number (%) of identifiable cell types in the percoll fractions (Fr) was as follows:

| Fr 2/3; | LL,66; | LGL,47; | SL,22; | M,6; | N,0 |
| Fr4; | LL,23; | LGL,3; | SL,76; | M,0; | N,1 |
| Fr5; | LL,0; | LGL,0; | SL,96; | M,0; | N,1 |
| Fr6; | LL,0; | LGL,0; | SL,88; | M,0; | N,2 |

Similar distributions of cell subpopulations were obtained upon repeat fractionation of PBMC before or following activation by viral antigens; the majority of LGL's were recovered from Fr $\frac{2}{3}$, whereas Fr5 and 6 consisted of enriched SL's.

(c) 4-Hour Chromium-51 Release Test

Target cells in a 0.2 ml volume were labelled for 1 hour at 37° C. with 200 μCi of $^{51}$Cr as sodium chromate (NA$_2$ $^{51}$CrO$_4$) (New England Nuclear, Boston, MA), washed 3 times in RPMI-FCS medium, resuspended in 10 ml of medium and incubated for a further one hour at 37° C. Cytotoxicity tests were performed in triplicate in round bottomed microtest wells (Catalogue 76-042-03, Flow Laboratories, Inc., McLean, VA). Effector cells (0.1 ml per well) were incubated with target cells (0.1 ml per well) at ratios of 20 to 1, 10 to 1, and 5 to 1 and the plates incubated at 37° C. for 4 hours in a humidified 5% CO$_2$ atmosphere. The plates were then centrifuged at 200 g for 5 minutes and 0.1 ml of the supernatant removed and counted for radioactivity in a gamma spectrophotometer. The percent chromium-51 release was determined for each group following subtraction of the spontaneous release, and the percent cytotoxicity calculated by the formula:

Percent Cytotoxicity =

$$\frac{(\text{Test release}) - (\text{Spontaneous release})}{100 - (\text{Spontaneous release})} \times 100$$

The background percent release during the 4-hour incubation period ranged from 5 to 10 percent for K562 and RAJ1 target cells and between 5 and 18 percent for A375, COLO205 and SW742 targets. Statistical analysis was performed by Student's 't' test where appropriate.

II.

Monocyte Mediated Cytotoxicity (a) Target Cells

The target cells used in the monocyte mediated cytotoxicity assay were the adherent human melanoma cell line A375 maintained as described above. The cells were labeled during overnight incubation in the presence of fresh media containing 0.3 μCi/ml $^{125}$IUdR. Cells were trypsinized and washed prior to use in the cytotoxicity assay.

(b) Effector Cells.

PBMC were isolated from Red Cross Buffy Coats using ficoll-hypaque density gradients described above. Monocytes, separated from PBMC on Percoll density gradients [See, Colotta et al. *J. Immunol.*, 132, 936 (1984)], were washed three times in RPMI medium and plated in 96 well flat bottom microtiter plates at a density of $2 \times 10^5$ monocytes/well. Nonadherent cells were removed by washing three times with warm RPMI after one hour incubation at 37°, 5% $CO_2$.

(c) Monocyte Cytotoxicity Assay

The cytotoxicity assay was performed as previously described [See, Klinerman, E. S., et al J. Clinm. Invest. 72, 304 (1983)]. Briefly, monocytes were incubated with antigen overnight; antigen was removed and $10^4$ labeled target cells were added to each well. Effector and target cells were incubated at 37°, 5% $CO_2$ for three days. Cytotoxicity was assessed by determining the residual adherent cell associated radioactivity. The cultures were washed three times, lysed in 50 $\mu$l 0.5M NaOH, and the cell lysate was absorbed onto cotton swabs that were then counted in a gamma spectrophotometer. The percent cytotoxicity was calculated by the formula:

$$\% \text{ Specific Cytotoxicity} = \frac{\text{cpm in target cells cultured with control monocytes} - \text{cpm in target cells cultured with test monocytes}}{\text{cpm in target cells cultured with control monocytes}} \times 100$$

III.

Anti-Human Interferon Sera

Sheep anti-human leukocyte IFN globulin that has a high neutralization titer against IFN$\alpha$ ($7.5 \times 10^5$ units/ml) and a low titer against IFN$\beta$ ($2 \times 10^3$ units/ml) was prepared as described [See, Dalton et al., *Methods in Enzymology*, 79, 561 (1981)]. Sheep anti-human fibroblast IFN$\beta$ globulin with $1.2 \times 10^4$ neutralizing units/ml was prepared following similar procedures using human fibroblast IFN (SA = $1 \times 10^6$ U/mg protein) that was purchased from the Rega Institute (Leuven, Belgium) as immunogen. Monoclonal mouse anti-human IFN$\gamma$ ascitic fluid ($1.2 \times 10^6$ neutralizing units per ml) was purchased from Meloy Laboratories (Springfield, VA 22151, USA). Control antisera for the sheep globulins were prepared by immunizing the sheep with contaminants which had been removed for the interferon preparations during purification, and a nonimmune ascites fluid was the control for the anti-human IFN$\gamma$. The following IFNs were used as specificity controls for the antisera: human leukocyte interferon (IFN-$\alpha$)(PIF 7901), produced in peripheral blood leukocytes stimulated with Sendai virus and partially purified to a specific activity (SA) of $1 \times 10^6$ units/mg protein, was a gift from Kari Cantell, State Serum Institute, Helsinki, Finland; human fibroblast IFN (IFN-$\beta$), SA = $1 \times 10^6$ units/mg protein, was obtained from the Rega Institute (Leuven, Belgium); IFN-$\gamma$, produced in human peripheral blood leukocytes induced with A23187 and mezerine (SA = $>1 \times 10^6$ units/mg protein), was obtained from Meloy Laboratories (Springfield, VA 22151, USA).

IV.

Assay for Interferon

The antiviral activity of the IFN was determined in WISH cells seeded in microtiter plates challenged with encephalomyocarditis virus (multiplicity of infection = 0.3), using modifications of previously described methods (35, 36). Interferon titers are expressed in terms of appropriate reference standards for human IFNs distributed by the Research Resources Branch, National Institutes of Allergy and Infectious Diseases, Bethesda, MD (HuIFN$\alpha$, G-023-901-527; HuIFN$\beta$, G-023-902-527; HuIFN$\gamma$, Gg 23-901-530).

V.

Synthesis and Purification of Influenza Virus Proteins Expressed in *E. Coli*

Influenza A virus-specific polypeptides were synthesized using the pAS1 *E. coli* expression vector described previously [See, e.g., Rosenberg et al., *Methods in Enzymology*, 101, 123 (1983); Shatzman et al., Experimental Manipulation of Gene Expression, M. Inove (Ed.) Academic Press (N.Y.), p. 1 (1983); Young et al., *Proc. Natl. Acad. Sci., U.S.A.*, 80, 6105 (1983)]. pAS1 is available without restriction from the American Type Culture Collection, Rockville, Md., under accession number ATCC 39261. Briefly, plasmids containing cDNA copies of the viral RNAs of A/PR/8/34 virus [See, Young et al., The Origin of Pandemic Influenza Virus, Laver (Ed.), Elsevier Press, Amsterdam, p. 120 (1983)] were manipulated according to the methods described in Maniatas et al., "Molecular Cloning", Cold Spring Harbor Laboratory (1982); to obtain expression of the following products: the 230 amino acid coding sequence of NS1 [See, Young et al., *Proc. Natl. Acad. Sci.*, U.S.A. cited above] and NS2 nonstructural proteins; C7, the mature HA sequence containing both HA1 and HA2; $\Delta$7, the HA1 sequence and the N-terminal 69 amino acids of the HA2 sequence; C36, the 222 amino acid HA2 sequence; C13, the N-terminal 81 amino acids of NS1 fused to HA2; $\Delta$13, the N-terminal 81 amino acids of NS1 fused to the N-terminal 69 amino acids of HA2; M45, the N-terminal 81 amino acids of NS1 fused to the matrix protein; M30, the N-terminal 81 amino acids of NS1 fused to the C-terminal 50 amino acids of the matrix protein; and M42, the N-terminal 81 amino acids of NS1 fused to the N-terminal 90 amino acids of the matrix protein and 86 amino acids derived from an open reading frame in the tetracycline resistance region.

A detailed description of the constructions of plasmids containing NS1, NS2, C7, $\Delta$7, C13, $\Delta$13, M45, M30 and M42 and the tetracycline resistance region is found in SmithKline Beckman Corporation, European Patent Application Publication No. EP-O-176,493,A2, the entire disclosure of which is hereby incorporated by reference.

The bacteria containing the plasmids encoding the proteins described above were grown and induced to synthesize these polypeptides [See, Rosenberg et al., Shatzman et al., and Young et al., *Proc. Natl. Acad. Sci.* cited above]. Total bacterial cell extracts were prepared following lysozyme treatment, sonication, and centrifugation. The NS1 protein was contained in the supernatant fraction and purified as described previously [See, Young et al., *Proc. Natl. Acad. Sci.* cited above]. All other influenza virus proteins produced in this manner were contained in the pellet fraction following centrifugation. These proteins were further purified by two 0.1% deoxycholate extractions and one extraction with 1% Triton X-100 to remove contaminating *E. coli* proteins. The viral polypeptide aggregates were then solubilized in 4M urea at 4° C. for 30 minutes. They were then dialyzed extensively against 50 mM Tris-HCL, pH 8.0, 1 mM ethylenediamine tetraacetic acid to remove the urea. Following this treatment the proteins remained soluble and were greater that 80% pure as determined by Coomassie blue staining of samples electrophoresed on SDS-polyacrylamide gels.

Mock protein preparations of both the supernatant and pellet fractions were prepared in parallel from the same *E. coli* strain containing the expression vector without influenza virus sequences. These samples served as control preparations in several experiments.

RESULTS

I.

Effect of Cloned Influenza Viral Gene Products on Natural Cytotoxicity

The proteins derived from influenza A virus cDNAs expressed in *E. coli*, as described above, included NS1, NS2, the HA (C7, Δ7, C36), HA sequences fused to the N-terminal 81 amino acids of NS1 (C13, Δ13), and the matrix protein fused to the N-terminal 81 amino acids of NS1 (M45, M42, M30). These purified antigen preparations were assayed for their effect on human nylon wool non-adherent PBMC natural cytotoxicity. In most studies the K562 and the A375 target cell lines were used to assay for natural cytotoxicity.

Initial experiments were performed using purified proteins at concentrations of 50 and 10 $\mu$g/ml. Following incubation with PBMC for 18 hours, the cells were harvested, and the overnight supernatant collected and stored at 4° for IFN assay. The cytolytic activity of PBMC against A375 and K562 target cells is given in Table 1. As can be seen in Table 1, several of the viral antigens described above were shown to significantly enhance natural cytotoxicity (P= <0.001). These included the NS1 antigen and protein derivatives containing the first 81 amino acids of NS1. In particular, NS1, C13, Δ13, M42 and M45 antigens were potent augmenters of human natural cytotoxicity; NS1 antigen titrating down to 1 $\mu$g/ml concentration (Table 1). M30 antigens also augmented human natural cytotoxicity. In addition, supernatants from overnight cultures which showed enhanced cytotoxicity contained detectable, and often high interferon (IFN) levels (80 to 1280 IFN Units/ml). Antigens containing the entire HA molecule (C7), a truncated version of this molecule (Δ7) or the HA2 amino acid sequence (C36) failed to significantly augment natural cytotoxicity or induce IFN in PBMC cultures.

In view of these findings, further studies were undertaken to establish more precisely the specificity of the activated cytotoxic effectors, and the conditions under which augmentation optimally occurs. Effector lymphocytes incubated with NS1 protein (10 $\mu$g/ml) showed a significant increased in cytotoxicity (P= <0.001), against a wide variety of target cells including K562, RAJI, COLO205 and SW742 cell lines. Again enhanced natural cytotoxicity correlated with high levels of IFN (1280 Units/ml) which was detected in supernatants derived from PBMC cultured with NS1 protein. Also, PBMC exposed to NS1 antigen for either 30 minutes or 2 hours, washed 3 times with RPMI-FCS medium to remove residual antigen, and incubated overnight at 37° prior to testing against tumour target cells, showed a similar enhancement of cytotoxicity (Table 2). In this instance, the antiviral IFN titer in the supernatant increased proportionally with the time of exposure of PBMC to NS1 antigen.

Although analysis of proteins by polyacrylamide gel electrophoresis showed the preparation to be greater than 80% pure for the influenza virus component, the possibility that contaminating components derived from the bacterial culture were, in part or whole, responsible for augmentation of natural cytotoxicity and IFN production was considered. The results of several experiments suggest that protein contaminants derived from the bacteria were not responsible for enhancing natural cytotoxicity, since preparations which augment NK activity (C13, Δ13, M45, M30) and those which had no effect on NK activity (C7, Δ7 C36) were purified by the same procedure and contained the same minor protein contaminants. However, to investigate this further, mock antigen preparations were prepared either from the bacteria used for expression of the gene, or bacteria which contained the plasmid vector minus the influenza gene sequence. Mock antigen preparations derived either from the bacterial supernatant (mock NS1 preparation) or the insoluble fraction of the bacteria failed to significantly augment natural cytotoxicity or induce IFN; the level of endotoxin contamination present in these mock preparations was similar to that of the viral proteins which was usually less that 50 ng/ml, making it unlikely that free endotoxin was responsible for enhancing natural cytotoxicity or inducing IFN. In subsequent experiments using a commercially prepared *E. coli* endotoxin (0127:B8; Difco Laboratories, Detroit, MI) significant activation of natural cytotoxicity or the production of IFN upon overnight incubation with PBMC was not observed. Moreover, experiments were performed in the presence of polymyxin B, (which is known to bind to the lipid A portion of the endotoxin molecule, neutralizing many endotoxin-mediated effects, such as its capacity to activate macrophages to become tumoricidal). Antigen preparations were pretreated with polymyxin B (40 $\mu$g/ml final concentration) for 90 minutes at 37° prior to their addition to PBMC cultures. Following overnight incubation the recovered PBMCs were assayed for natural cytotoxicity against K562 and A375 target cells, and the results for A375 targets, using NS1, C13 and Δ13 antigens indicate that the presence of polymyxin B failed to influence the ability of antigen preparations to stimulate natural cytotoxicity, or to significantly reduce the level of IFN induced.

The preparations used in the studies described above also contained residual fragments of bacterial-derived nuclei acid; however, these were present in similar quantities in both 'mock' and antigen preparations, making it unlikely that these molecular species were responsible for stimulating PBMC natural cytotoxicity. In order to eliminate the possibility that low molecular weight contaminants contributed to the production of interferon and augmentation of natural cytotoxicity, NS1 antigen preparations were passed through Centricon membrane filters (Amicon Corp., Lexington, MA) which retain substances with a molecular weight greater than 10,000 daltons. It was observed that the ability to augment natural killer cells was present only in the retentate fraction, and such observation suggests that the low molecular weight substances were not responsible for the observed stimulation.

II.

The Nature of the Effector Cells Responding to NS1 Antigen

Limited studies were undertaken to ascertain the PBMC effector cell population responding to cloned viral antigen stimulation. It was noted in several experiments that nylon wool non-adherent lymphocytes could be augmented more readily by NS1 antigen than unfractionated PBMC. Table 3 illustrates this finding, thereby indicating that nylon wool adherent PBMC in some way interferes with IFN production and the enhancement of natural cytotoxicity. Percoll discontinuous gradient separation was used to determine further the characteristics of lymphocytes responding to NS1 antigen. Following fractionation, the combination $\frac{3}{5}$ fraction, 4 fraction, 5 fraction, 6 fraction and a pool of fractions 4, 5 and 6 where cultured for 18 hours at 37° in the presence or absence of NS1 antigen. (See Materials and Methods portion of Examples for details of cell populations present in percoll fractions.) The cells were subsequently harvested and assayed for cytotoxicity against A375 and K562 targets, and the culture supernatant collected for IFN determination. Interferon production was maximum in cultures of lymphocytes recovered from the low density region of the gradient ($\frac{3}{5}$ fraction). Lymphocytes recovered from this fraction also showed maximum augmentation of natural cytotoxicity against both A375 and K562 cells. PBMC recovered from the high density regions of the gradient (4 fraction, 5 fraction and 6 fraction) failed to produce significant levels of interferon and showed no increased cytolytic activity following co-cultures with NS1.

To define further the characteristics associated with activated PBMC, nylon wool non-adherent PBMC were exposed to NS1 antigen for 18 hours at 37° and subsequently fractionated on 7-step percoll gradients. The results showed that the cytotoxicity of NS1 activated lymphocytes is recoverable in the $\frac{3}{5}$ fraction (highly enriched for LGL's—See Materials and Methods) and 4 fraction (low density regions) of percoll gradients, whereas lymphocytes recovered from the high density fraction (5 fraction), were highly enriched for SL's (See Materials and Methods) and showed no increased cytotoxicity towards tumour targets.

III.

Identity of Interferon Produced by Viral Protein Antigens Stimulated PBMC

The IFN generated from PBMC cultured with NS1 antigen or constructs containing a sequence of the NS1 gene product was identified antigenically by neutralization with specific antisera. In all these assays, antiserum was used at a dilution capable of neutralizing in excess of 5000 units of each species of IFN. Culture supernatant from either NS1 or C13 antigen-stimulated PBMC was incubated for one hour at 37° with each of the antisera and then assayed for residual antiviral activity. Antisera against IFN$\beta$ and IFN$\gamma$ failed to reduce significantly the interferon titer of the culture supernatants; whereas, anti-IFN$\alpha$ antisera neutralized in excess of 90% of the antiviral activity (Table 4). In this and subsequent experiments, IFN$\alpha$ antiserum failed to cause complete neutralization of the interferon; however, a combination of antisera specific for IFN$\alpha$ and IFN$\gamma$ (but not IFN$\alpha$ and IFN$\beta$) neutralized all the antiviral activity. Thus, it was concluded that although the majority of interferon produced as a result of stimulation with NS1 and C13 influenza viral antigens is IFN$\alpha$, a portion (less than 10%) of the interferon present appears to be human IFN$\gamma$.

IV.

Evidence that Antigen Generated Interferon Mediates Enhancement of Natural Cytotoxicity Although both IFN$\alpha$ and low levels of IFN$\gamma$ were generated when PBMC were co-cultured with purified influenza NS1 viral antigen, it remained to be established whether these lymphokines alone or together were responsible for the elevation of natural cytotoxicity. PBMC cultures were therefore incubated for 18 hours at 37° with NS1 antigen (10 $\mu$g/ml final concentration) with or without the addition of specific anti-IFN$\alpha$ or anti-IFN$\gamma$ antiserum or the appropriate control sera. The results of a representative experiment, using A375 and K562 cells as targets show that in the presence of anti-IFN$\alpha$ but not anti-IFN$\gamma$ antiserum, enhancement of natural cytotoxicity by NS1 antigen is almost completely neutralized. The control antisera did not influence the degree of enhancement of natural cytotoxicity mediated by NS1 antigen. Antiviral interferon assays, performed on the 18-hour culture supernatants confirmed the absence of demonstrable IFN in the cultures treated with anti-IFN$\alpha$ antiserum; whereas significant IFN activity was detectable in culture supernatant where PBMC showed enhanced natural cytotoxicity. It was concluded from these experiments that the generation of alpha interferon is responsible for potentiating natural cytotoxicity in this system.

V.

Evidence that NS1 and C13 Antigen Stimulate Human Monocyte Tumoricidal Activity Table 5 represents a preliminary experiment wherein NS1 and NS1 fusion protein C-13 were assayed for their ability to stimulate human monocyte tumoricidal activity following the experimental protocol described above. (See Materials and Methods)

The results indicated in Table 5 show that tumoricidal activity was detected in both the presence and absence of polymyxin B suggesting that the activity was not due entirely to the presence of LPS (a potent stimulator of monocyte cytotoxicity). These results suggest that NS1 gene products may modulate other effector mechanisms in addition to enhancing NK activity.

TABLE 1

| | | Natural Cytotoxicity and IFN Production by Human PBMC Exposed to Influenza Virus Gene Products | | | | | | |
|---|---|---|---|---|---|---|---|---|
| | Antigen | % Cytotoxicity[1] Target Cell Line | | | | | | |
| Exp. | (conc. | A375 | | | K562 | | | IFN |
| No. | $\mu$g/ml) | E:T  20:1 | 10:1 | 5:1 | 20:1 | 10:1 | 5:1 | (units/ml) |
| 1. | — | 4 | 2 | 0 | 25 | 12 | 5 | $\leq 1$ |

TABLE 1-continued

Natural Cytotoxicity and IFN Production by Human PBMC Exposed to Influenza Virus Gene Products

| Exp. No. | Antigen (conc. µg/ml) | % Cytotoxicity[1] Target Cell Line A375 E:T 20:1 | 10:1 | 5:1 | K562 20:1 | 10:1 | 5:1 | IFN (units/ml) |
|---|---|---|---|---|---|---|---|---|
| | NS1 (10) | 31 | 14 | 7 | 60 | 41 | 24 | 1280 |
| | M30 (10) | 9 | 2 | 1 | 48 | 33 | 19 | 16 |
| | M42 (10) | 30 | 16 | 3 | 62 | 41 | 24 | ≧512 |
| | M45 (10) | 26 | 11 | 3 | 64 | 40 | 20 | ≧512 |
| 2. | — | 7 | 3 | 3 | 35 | 22 | 7 | ≦1 |
| | NS1 (10) | 28 | 10 | 8 | 51 | 36 | 19 | 8 |
| | M42 (10) | 42 | 25 | 15 | 50 | 37 | 21 | 250 |
| | M45 (10) | 20 | 11 | 5 | 48 | 30 | 15 | 8 |
| | C13 (10) | 30 | 17 | 5 | 47 | 32 | 16 | 80 |
| 3. | — | NT[2] | NT | NT | 50 | 37 | 20 | ≦1 |
| | C13 (50) | NT | NT | NT | 68 | 53 | 32 | 512 |
| | M30 (50) | NT | NT | NT | 60 | 47 | 26 | 4 |
| | Δ13 (10) | NT | NT | NT | 63 | 54 | 42 | ≧512 |
| | NS2 (10) | NT | NT | NT | 54 | 37 | 22 | ≦1 |
| | NS1 (50) | NT | NT | NT | 69 | 64 | 50 | 1280 |
| | NS1 (10) | NT | NT | NT | 68 | 61 | 43 | 512 |
| | NS1 (2) | NT | NT | NT | 66 | 55 | 36 | 32 |
| | NS1 (1) | NT | NT | NT | 66 | 52 | 33 | 8 |

[1]4 hour $^{51}$Cr-release assay. Cytotoxicity values underlined indicate statistically significant (P = 0.001) augmentation of natural cytotoxicity.
[2]NT = Not Tested.

TABLE 2

Natural Cytotoxicity and IFN Production by Human PBMC Following Exposure to NS1 Antigen

| Antigen | Exposure (hr):[2] | % Cytotoxicity[1] E:T Ratio 20:1 | 10:1 | 5:1 | IFN (units/ml) |
|---|---|---|---|---|---|
| — | | 50.4 | 37.1 | 19.9 | 0 |
| NS1 (10 µg/ml) | 18 hour | 67.8 | 61.3 | 43.3 | 512 |
| NS1 (10 µg/ml) | 2 hour | 70.3 | 57.6 | 38.8 | 128 |
| NS1 (10 µg/ml) | ½ hour | 67.8 | 53.7 | 67.4 | 64 |

[1]4-hour $^{51}$Cr-release assay. Cytotoxicity values underlined indicate statistically significant (P = <0.001) augmentation of natural cytotoxicity against K562 target cells.
[2]Nylon wool non-adherent PBMC were incubated at 37° C. with or without the addition of NS1 (10 µg/ml) for ½ hour or 2 hours, washed three times (RPMI-FBS) and reincubated at 37° C. for 17½ hours and 16 hours respectively. Similar cultures were incubated at 37° C. with or without NS1 (10 µg/ml) for 18 hours.

TABLE 3

Unfractionated vs. Nylon Wool Non-Adherent PBMC Natural Cytotoxicity - Augmentation by NS1 Antigen

| Target | 18 hour/Culture PBMC | Antigen | Experiment 1 % Cytotoxicity[1] | IFN[2] | Experiment 2 % Cytotoxicity[1] | IFN[2] |
|---|---|---|---|---|---|---|
| A375P | Unf | — | 1.3 | ≦1 | 0 | ≦1 |
| | | NS1 | 5.5 | ≦1 | 1.5 | ≦5 |
| | NW-EL | — | 1.1 | ≦5 | 3.3 | ≦1 |
| | | NS1 | 22.2 | 640 | 41.2 | 320 |
| K562 | Unf | — | 7.3 | ≦1 | 9.3 | ≦1 |
| | | NS1 | 17.3 | ≦1 | 9.1 | ≦5 |
| | NW-EL | — | 30.8 | ≦5 | 28.8 | ≦1 |
| | | NS1 | 57.8 | 640 | 60.9 | 320 |

[1]4-hour $^{51}$Cr-release assay. Underlined values indicate statistically significant (P = <0.001) augmentation of natural cytotoxicity. (E:T = 10:1).
[2]Units of IFN per ml. of culture supernatant.

TABLE 4

Antigenic Identification of NS1 and C13 Generated HuIFN

| Antigen | Residual Interferon Units per Milliliter Antisera[1] — | α | β | γ | β + γ | α + β | α + γ |
|---|---|---|---|---|---|---|---|
| NS1-SN[2] | 1024 | 32 | 512 | 512 | 512 | 4 | 0 |
| C13-SN | 256 | 8 | 256 | 128 | 256 | 8 | 0 |
| C13-SN | 512 | 4 | 512 | 512 | NT[4] | NT | NT |
| Cont. [3]IFNα | 4000 | 0 | 4000 | 4000 | NT | NT | NT |
| Cont. IFNβ | 512 | 128 | 0 | 512 | NT | NT | NT |
| Cont. IFNγ | 512 | 512 | 512 | 1 | NT | NT | NT |

[1]Antisera specific for human IFNα, IFNβ or IFNγ used alone or in combination.
[2]18 hour culture supernatant from PBMC incubated with 10 µg/ml antigen.
[3]Specificity controls for IFNα, IFNβ, IFNγ.
[4]NT = Not Tested

TABLE 5

Stimulation of Human Monocyte Cytotoxicity
By Influenza Virus Antigens NS1 & C13

| | Stimulus | | Percent Cytotoxicity of A375 Tumor Cells | |
|---|---|---|---|---|
| | | | No Rx | Polymyxin B[a] |
| NS1 | 25 μg/ml | | 76.6 | 76.5 |
| | 5 | | 75.7 | 68.6 |
| | 1 | | 77.3 | 22.4 |
| | 0.2 | | 24.3 | 13.5 |
| C13 | 25 μg/ml | | 80.0 | 72.5 |
| | 5 | | 71.8 | 15.6 |
| | 1 | | 16.3 | 0.6 |
| | 0.2 | | 12.5 | 0 |
| LPS | 10 ng/ml | | 85.8 | 2.6 |
| | 1 | | 68.8 | 1.9 |
| | 0.1 | | 27.7 | 8.0 |
| | 0.01 | | 4.7 | 9.6 |
| | 0.001 | | 1.9 | 6.1 |
| Polymyxin B[a] | 20 μg/ml | | 0 | N.D.[b] |

[a]Stimulus treated with 40 μg/ml of Polymyxin B at 37° for 1 hr prior to addition to human monocyte culture (1:2 dilution).
[b]N.D. = Not done

EXAMPLE

PARENTERAL PHARMACEUTICAL COMPOSITION

A pharmaceutical composition of this invention suitable for parenteral administration is prepared by admixing 25 mg of NS1 in a solution containing sufficient phosphate buffer to adjust the pH to approximately 6.0; then adding sufficient sodium chloride to render the solution isotonic, and adjusting the solution to final volume with water.

EXAMPLE

PHARMACEUTICAL COMPOSITION FOR ADMINISTRATION BY INHALATION

A pharmaceutical composition of this invention for administration by inhalation is prepared according to the following for an aerosol container with a capacity of 15–20 ml: Dissolve 10 mg of NS1 with ethanol (25% to adjust to volume), and disperse such in a 40:60 ratio of Freon 12: Freon 114 and 0.1% Span 85, and put such dispersion in an appropriate aerosol container adapted for either intranasal or oral inhalation administration.

What is claimed is:

1. A method of modulating the immune response in a human, or other animal, in need thereof by inducing the production of leukocyte IFN which comprises administering an effective, leukocyte interferon production inducing amount of NS1 to such human or animal.

2. The method of claim 1 which comprises administering the product of the N-terminal 81 amino acids of the NS1 coding sequence fused to the HA2 coding sequence.

3. The method of claim 1 which comprises administering the product of the N-terminal 81 amino acids of the NS1 coding sequence fused to the N-terminal 69 amino acids of the HA2 coding sequence.

4. The method of claim 1 which comprises administering the product of the N-terminal 81 amino acids of the NS1 coding sequence fused to the matrix protein coding sequence.

5. The method of claim 1 which comprises administering the product of the N-terminal 81 amino acids of the NS1 coding sequence fused to the C-terminal 50 amino acids of the matrix protein coding sequence.

6. The method of claim 1 which comprises administering the product of the N-terminal 81 amino acids of the NS1 coding sequence fused to the N-terminal 90 amino acids of the matrix protein coding sequence.

7. The method of claim 1 wherein the NS1 is administered in oral dosage form.

8. The method of claim 1 wherein the NS1 is administered in parenteral dosage form.

9. The method of claim 8 wherein from about 0.05 to 1.0 mg per kilogram of total body weight of the NS1 is administered.

10. The method of claim 9 wherein from about 0.05 to about 0.25 mg/kg of total body weight of the NS1 is administered.

11. The method of claim 1 wherein the NS1 is administered by inhalation.

* * * * *